(12) United States Patent
Persohn et al.

(10) Patent No.: US 6,409,515 B1
(45) Date of Patent: Jun. 25, 2002

(54) IMAGING SYSTEM PHANTOM

(75) Inventors: James L. Persohn, Nashotah; Donald E. Kosak, Menomonee Falls; Lance L. Lightfoot, Waukesha, all of WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 09/366,672

(22) Filed: Aug. 3, 1999

(51) Int. Cl.$^7$ .................................................. G09B 23/28
(52) U.S. Cl. ........................................ 434/262; 434/267
(58) Field of Search .................. 434/159, 160, 434/171, 167, 146, 262, 267; 496/115, 116; 273/153 R, 157 R; 324/307, 308, 309

(56) References Cited

U.S. PATENT DOCUMENTS

| | | | |
|---|---|---|---|
| 3,726,027 A | * | 4/1973 | Cohen et al. ................ 434/160 |
| 4,529,201 A | * | 7/1985 | Nadel ...................... 273/157 R |
| 4,575,088 A | * | 3/1986 | Peek ........................ 273/157 R |
| 4,618,978 A | | 10/1986 | Cosman |
| 4,644,276 A | | 2/1987 | Sierocuk et al. |
| 4,794,024 A | * | 12/1988 | Crowell et al. .............. 434/171 |
| 4,957,291 A | * | 9/1990 | Miffitt et al. ............ 273/157 R |
| 5,057,024 A | * | 10/1991 | Sprott et al. ................ 434/146 |
| 5,338,033 A | * | 8/1994 | Serrano .................. 273/157 R |
| 5,386,993 A | * | 2/1995 | Aspan .................... 273/157 R |
| 5,620,324 A | * | 4/1997 | Rettke ........................ 434/160 |

FOREIGN PATENT DOCUMENTS

GB    1098615    1/1968

\* cited by examiner

Primary Examiner—Sam Rimell
(74) Attorney, Agent, or Firm—Carl B. Horton, Esq.; Armstrong Teasdale LLP

(57) ABSTRACT

A phantom for a real-time interactive imaging system is described. The phantom includes a plurality of segments having unique identifiers, the segments joining together to form a polyhedron around an inner plate. In one embodiment, the inner plate has a unique identifier and two inner blocks positioned orthogonally upon it, each inner block also having a unique identifier. The phantom provides a variety of uniquely identified surfaces, angles and edges for scanning practice in a real-time interactive environment, and enables the imaging system user to verify image correctness and annotation.

29 Claims, 3 Drawing Sheets

IMAGING SYSTEM PHANTOM

BACKGROUND OF THE INVENTION

This invention relates generally to an imaging system and, more particularly, to a phantom for use with an imaging system.

Medical imaging systems include a source that emits signals (including but not limited to x-ray, radio frequency, or sonar signals), and the signals are directed toward an object to be imaged. The emitted signals and the interposed object interact to produce a response that is received by one or more detectors. The imaging system then processes the detected response signals to generate an image of the object.

With real-time interactive imaging systems, a user controls movement of system components in three-dimensional space while performing scans. Inexperienced operators often have difficulty in visualizing the object in threedimensional space and maneuvering the system in three dimensions while scanning. In addition, proper verification of image orientation and image annotation is difficult, particularly for double angle oblique scans acquired in real time.

BRIEF SUMMARY OF THE INVENTION

The present invention, in one aspect, is a phantom that facilitates training operators with respect to positioning the image system components, and includes an inner plate enclosed and supported by a plurality of segments which join together to form an icosahedron. Each segment includes a unique identifier, for example, an alphanumeric character. Two inner blocks are seated on the inner plate which, together with the inner blocks, indicate orthogonal planes (i.e. axial, sagittal, and coronal). The inner plate and inner blocks have unique identifiers that, together with the segment identifiers, are used to orient the imaging system source during imaging.

DETAILED DESCRIPTION OF THE INVENTION

Figure 1:
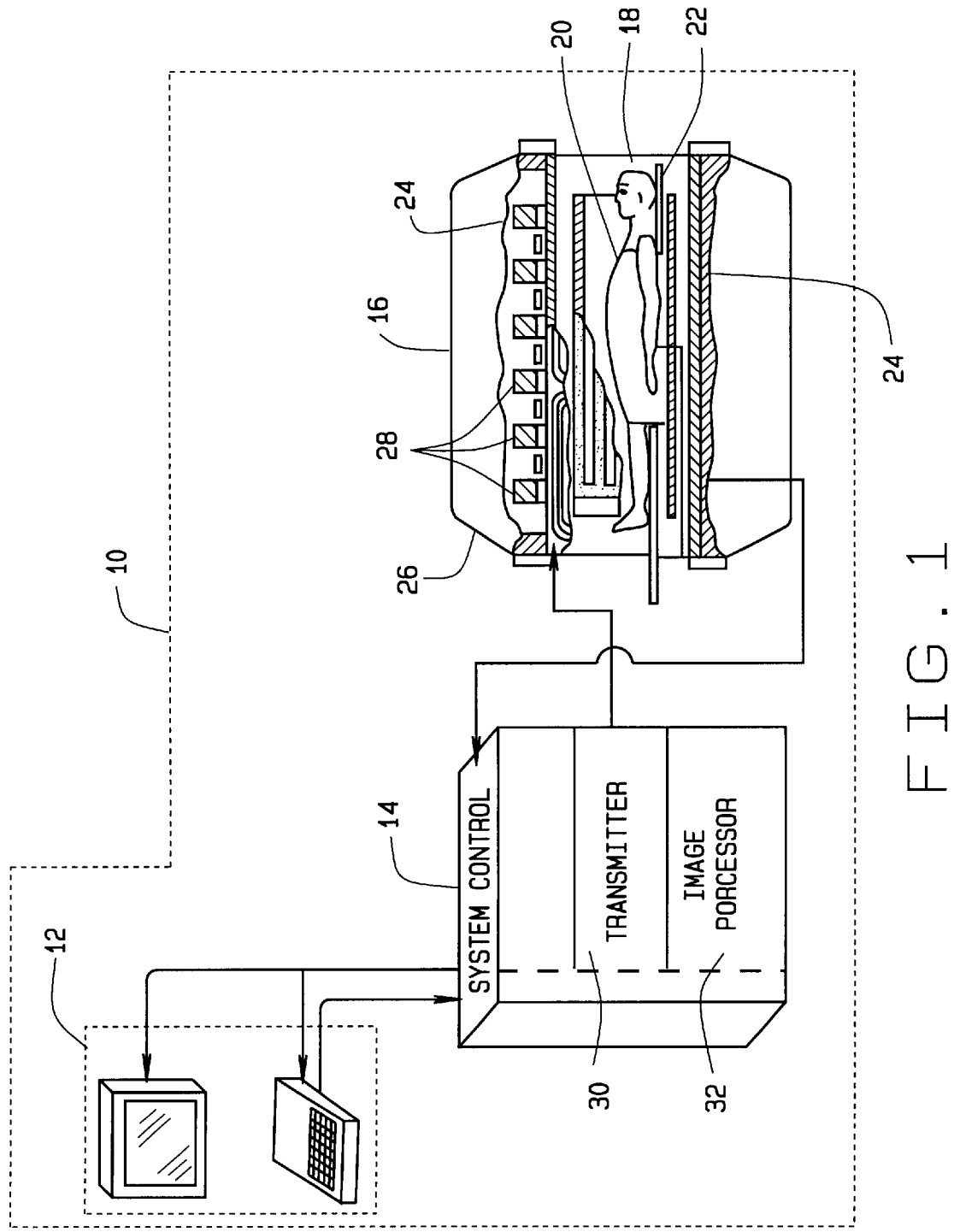
FIG. 1 is a pictorial view of an MRI imaging system.

Referring to FIG. 1, major components of an MRI imaging system 10 include an operator console 12 from which the operator controls imaging system 10. A system control 14 receives commands from the operator indicating the scan sequence to be performed and transmits imaging control signals to an MRI scanner 16. Within a cylindrical bore 18 of scanner 16, patient or object 20 is positioned on a table 22 and is surrounded by a magnetic coil or detector 24. Magnetic coil 24 is part of a magnet assembly 26, which also includes a polarizing magnet 28. Polarizing magnet 28 subjects object 20 to a uniform magnetic field. A transmitter or source 30 included in system control 14 transmits radio frequency pulses to magnet assembly 26. The resulting signals emitted by the excited spins in object 20 are picked up by magnetic coil 24, transmitted to system control 14 and reconstructed into an image by an image processor 32. The operator of imaging system 10 is able to view the image on console 12. If imaging system 10 is interactive in real time, the operator is able to view images and alter the scan sequence as it progresses.

Figure 2:
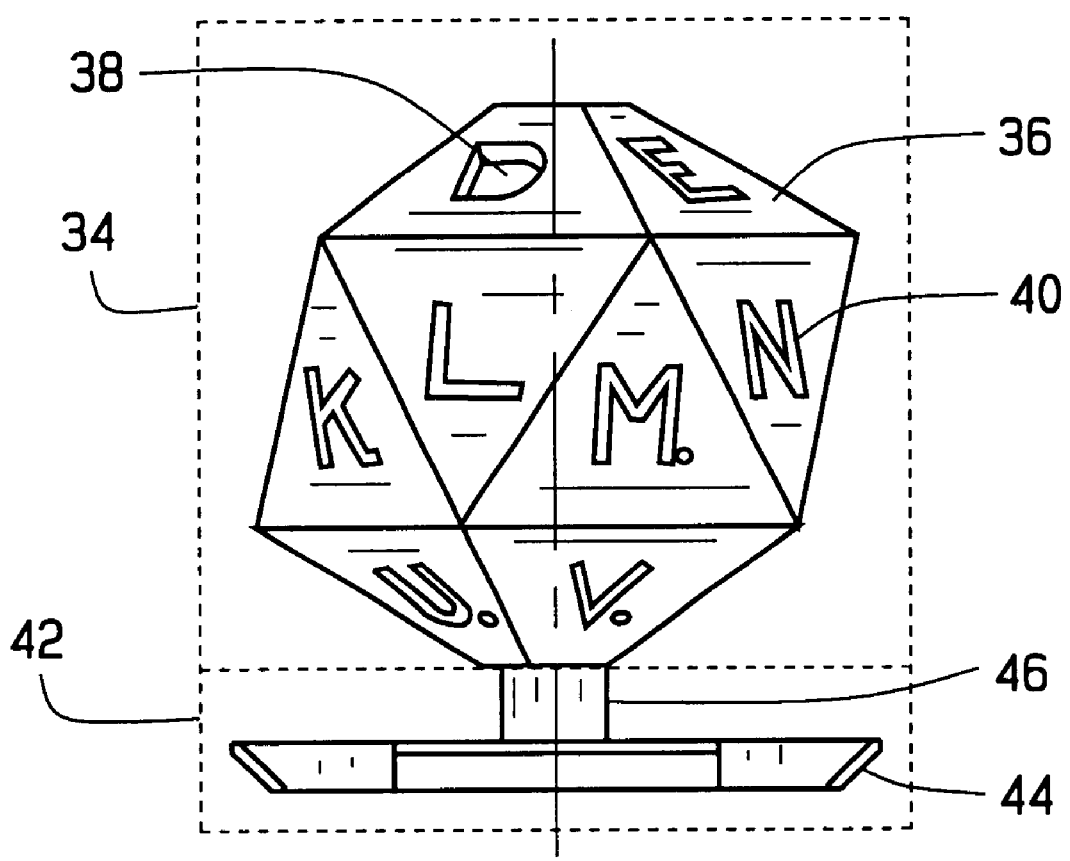
FIG. 2 is an elevational view of an embodiment of a phantom.

In one embodiment and as shown in FIG. 2, a phantom 34 for use with imaging system 10 includes twenty triangular segments or sides 36. Segments 36 are coupled together to form a substantially polyhedral shape enclosing a volume 38. Each segment 36 includes a unique segment identifier 40. Phantom 34 is coupled to and supported by a stand 42, which includes a base 44 and a support member 46.

Figure 3:
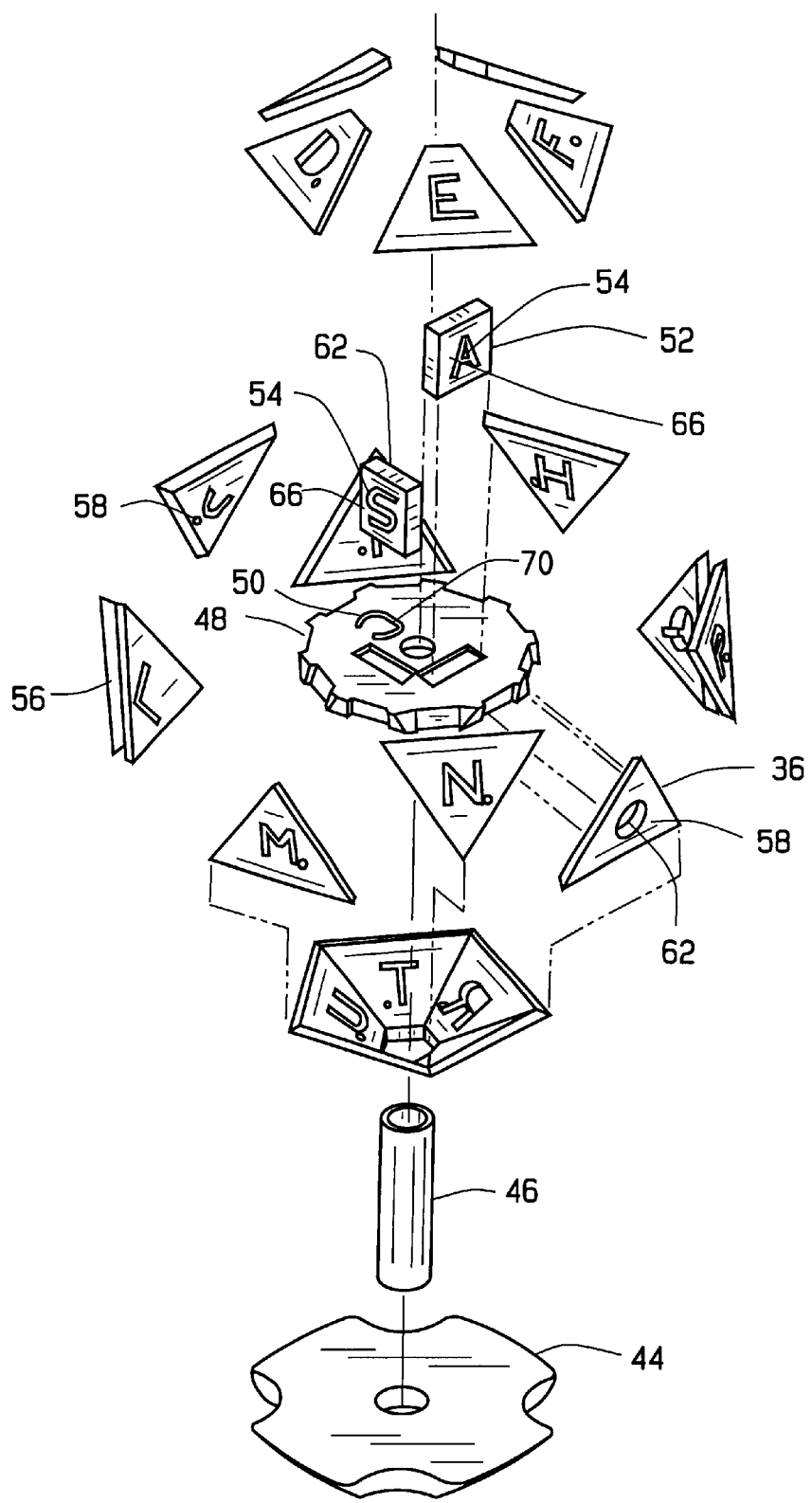
FIG. 3 is an exploded perspective view of the phantom shown in FIG. 2.

FIG. 3 is an exploded view of phantom 34. As shown in FIG. 3, phantom 34 includes an inner plate 48 surrounded by and connected to several segments 36. Inner plate 48 includes a unique plate identifier 50. Two inner blocks 52 are positioned over inner plate 48. Each inner block 52 includes a unique block identifier 54. Each segment identifier 40, block identifier 54 and plate identifier 50 includes an alphanumeric character 56 and also includes a period 58. Each segment identifier 40 outlines an opening 62 through the corresponding segment 36. In the same manner, each block identifier 54 outlines an opening 66 through the corresponding inner block 52, and plate identifier 50 outlines an opening 70 through inner plate 48.

Imaging quality often is enhanced, particularly in the case of an MRI imaging system, by submerging phantom 34 in liquid, e. g. water. Therefore, in one embodiment, a container (not shown) is configured to receive phantom 34 and stand 42. The container then is filled with a liquid, sealed and placed on table 22 for imaging. Segments 36, inner plate 48, inner blocks 52, and stand 42, in an exemplary embodiment, are fabricated from acrylic sheet and joined together with Weld-On 40 adhesive available from IPS Corporation, Compton, Calif. 90220.

When phantom 34 is in use, openings 62, 66 and 70 are visible from multiple directions and are used to identify the direction from which phantom 34 is being viewed. Inner blocks 52 and inner plate 48 are orthogonal to one another, thereby providing orthogonal axes for imaging system alignment purposes. For example, as shown in FIG. 3, block identifiers 54 and plate identifier 50 are denoted as "A.", "S." and "C." respectively, to indicate axial, sagittal and coronal planes. Stand 42 is configured to orient inner plate 48 horizontally when phantom 34 is positioned on table 22.

An imaging system user prepares for imaging by orienting phantom 34 on table 22 at a particular location relative to imaging system 10. Specifically, inner blocks 52 and inner plate 48 are aligned orthogonally to imaging system 10. In generating an image of phantom 34, an imaging system user orients source 30 relative to a particular segment 36, inner plate 48, and/or a particular inner block 52. The user then generates an image of segment 36, inner plate 48, and/or inner block 52 for comparison with the known configuration and orientation of phantom 34. In orienting source 30 to produce an image, the imaging system operator uses segment identifiers 40, plate identifier 50, and (if present in the particular embodiment) block identifiers 54 as guides in maneuvering in three dimensions. Based on the image generated, the operator can ascertain whether the desired positioning was achieved.

The above described phantom facilitates and shortens time needed for training imaging system operators, particularly for interactive real-time imaging systems. Specifically, the phantom provides a variety of surfaces, angles and edges in scanning locations known to the imaging system operator. The phantom enables an operator to practice scanning from many directions, or alternatively to generate images to verify an imaging system's image correctness and annotation.

Alternative embodiments of the phantom include segments 36, inner plate 48 and inner blocks 52 of shape and number other than those described above and that join together to form a polyhedron other than an icosahedron. Segment, plate and block identifiers other than alphanumeric characters followed by periods also can be used. Further, the phantom and stand can be fabricated from materials other than acrylic, such as other plastics. In addition, although the invention has been described occasionally with reference to a MRI system, the invention is not limited to use with MRI systems, and may be used with other types of imaging systems.

While the invention has been described in terms of various specific embodiments, those skilled in the art will recognize that the invention can be practiced with modification within the spirit and scope of the claims.

What is claimed is:

1. A phantom for use with an imaging system, said phantom comprising:
   a plurality of segments, each said segment coupled to at least one other said segment to enclose a volume, each said segment having a segment identifier outlining an opening through the segment, said segment identifier uniquely identifying said segment relative to other said segments;
   an inner plate positioned within said volume, said inner plate coupled to at least one said segment and having a plate identifier outlining an opening through said inner plate; and
   at least one inner block positioned within said volume, each said inner block disposed upon said inner plate and having a block identifier outlining an opening through said inner block.

2. A phantom for use with an imaging system, said phantom comprising:
   a plurality of segments, each said segment coupled to at least one other said segment to enclose a volume, each said segment having a unique segment identifier comprising at least one alphanumeric character such that each said individual segment is identified differently from all other said segments, at least one said segment comprising only three sides and only one alphanumeric character; and
   an inner plate positioned within said volume, said inner plate coupled to at least one said segment.

3. A phantom in accordance with claim 2 wherein said inner plate comprises a unique plate identifier.

4. A phantom in accordance with claim 3 further comprising at least one inner block positioned within said volume, each said inner block disposed upon said inner plate.

5. A phantom in accordance with claim 4 wherein each said inner block comprises a unique block identifier.

6. A phantom in accordance with claim 2 wherein each said segment identifier further comprises a period.

7. A phantom for use with an imaging system, said phantom comprising:
   a plurality of segments, each said segment coupled to at least one other said segment to enclose a volume, each said segment having a unique segment identifier;
   an inner plate positioned within said volume, said inner plate coupled to at least one said segment, wherein said inner plate comprises a unique plate identifier;
   at least one inner block positioned within said volume, each said inner block disposed upon said inner plate, wherein each said inner block comprises a unique block identifier outlining an opening through each said corresponding inner block.

8. A phantom in accordance with claim 7 wherein said plurality of segments form substantially a polyhedron.

9. A phantom in accordance with claim 8 comprising twenty segments.

10. A phantom in accordance with claim 8 wherein each said segment is substantially a triangle.

11. A phantom in accordance with claim 7 wherein said segments and said inner plate comprise a plastic material.

12. A phantom in accordance with claim 7 wherein said plate identifier outlines an opening through said inner plate.

13. A phantom in accordance with claim 7 wherein each said segment identifier outlines an opening through each said corresponding segment.

14. A phantom in accordance with claim 7 wherein said phantom comprises at least two said inner blocks substantially orthogonal to one another.

15. An imaging object for use with an imaging system, said imaging object comprising a phantom in accordance with claim 7 and a stand coupled to and supporting said phantom.

16. A phantom in accordance with claim 15 further comprising a container configured to receive said phantom and said stand.

17. A phantom in accordance with claim 7 wherein said phantom comprises at least one said inner block substantially orthogonal to said inner plate.

18. A phantom for use with an imaging system, said phantom comprising:
   a plurality of segments, each said segment coupled to at least one other said segment to enclose a volume, each said segment having a unique segment identifier; and
   an inner plate positioned within said volume, said inner plate coupled to at least one said segment and said inner plate having a unique plate identifier comprising at least one alphanumeric character.

19. A phantom in accordance with claim 18 wherein said plate identifier further comprises a period.

20. A phantom for use with an imaging system, said phantom comprising:
   a plurality of segments, each said segment coupled to at least one other said segment to enclose a volume, each said segment having a unique segment identifier;
   an inner plate positioned within said volume, said inner plate coupled to at least one said segment, said inner plate comprising a unique plate identifier;
   at least one inner block positioned within said volume, each said inner block disposed upon said inner plate, and said inner block having a unique block identifier comprising at least one alphanumeric character.

21. A phantom in accordance with claim 20 wherein each said block identifier further comprises a period.

22. An imaging object for use with an imaging system, said imaging object comprising:
   a phantom comprising a plurality of segments, each said segment coupled to at least one other said segment to enclose a volume, each said segment having a unique segment identifier, said phantom further comprising an inner plate positioned within said volume, said inner plate coupled to at least one said segment;
   a stand coupled to and supporting said phantom;
   a container configured to receive said phantom and said stand, said container comprising a means for sealing liquid inside said container.

23. An imaging object in accordance with claim 22 wherein the imaging system includes a table for supporting objects to be imaged and wherein said stand is configured to orient said inner plate horizontally as said phantom rests on the table.

24. An imaging object in accordance with claim 22 wherein said stand comprises a plastic material.

25. An imaging object in accordance with claim 22 wherein said stand comprises a base and a support member.

26. A phantom for use with an imaging system, said phantom comprising:

a plurality of segments, each said segment coupled to at least one other said segment to enclose a volume, each said segment having a segment identifier outlining an opening through the segment, said segment identifier uniquely identifying said segment relative to other said segments;

an inner plate positioned within said volume, said inner plate coupled to at least one said segment and having a plate identifier outlining an opening through said inner plate; and at least one inner block positioned within said volume, each said inner block disposed upon said inner plate and having a block identifier outlining an opening through said inner block;

wherein said openings outlined by said segment identifiers, said plate identifier, and said block identifier are visible from multiple directions.

27. A phantom in accordance with claim 26 wherein said phantom comprises at least one said inner block substantially orthogonal to said inner plate.

28. A phantom in accordance with claim 26 wherein said phantom comprises at least two said inner blocks substantially orthogonal to one another.

29. A phantom in accordance with claim 26 wherein said phantom comprises at least two said inner blocks, and each said block identifier uniquely identifies said inner block relative to other said inner blocks.

* * * * *